United States Patent
Baer et al.

(10) Patent No.: US 10,351,998 B2
(45) Date of Patent: Jul. 16, 2019

(54) PRE-MOISTENED WET WIPE PRODUCTS IN PERFORATED ROLL FORM MADE OF TISSUE BASED SUBSTRATES

(71) Applicant: GPCP IP Holdings LLC, Atlanta, GA (US)

(72) Inventors: Samuel C. Baer, Atlanta, GA (US); Steven L. Cavadeas, Franklin, WI (US); Kip K. Decker, Neenah, WI (US); Donald H. Wolfe, Atlanta, GA (US)

(73) Assignee: GPCP IP Holdings LLC, Altlanta, GA (US)

(*) Notice: Subject to any disclaimer, the term of this patent is extended or adjusted under 35 U.S.C. 154(b) by 0 days.

(21) Appl. No.: 15/468,384

(22) PCT Filed: Sep. 22, 2015

(86) PCT No.: PCT/US2015/051325
§ 371 (c)(1),
(2) Date: Mar. 24, 2017

(87) PCT Pub. No.: WO2016/048943
PCT Pub. Date: Mar. 31, 2016

(65) Prior Publication Data
US 2017/0211234 A1    Jul. 27, 2017

Related U.S. Application Data

(60) Provisional application No. 62/054,633, filed on Sep. 24, 2014.

(51) Int. Cl.
*A47K 7/00*    (2006.01)
*D21H 27/00*    (2006.01)
(Continued)

(52) U.S. Cl.
CPC ....... *D21H 27/007* (2013.01); *A47K 10/3818* (2013.01); *A61K 8/0208* (2013.01);
(Continued)

(58) Field of Classification Search
None
See application file for complete search history.

(56) References Cited

U.S. PATENT DOCUMENTS 6,578,731 B1 * 6/2003 Lewis ............... A47K 10/3818
221/46
2004/0099389 A1 * 5/2004 Chen ........................ D21F 9/00
162/134
(Continued)

FOREIGN PATENT DOCUMENTS

| WO | 9314267 A1 | 7/1993 |
| WO | 2007001837 A2 | 1/2007 |
| WO | 2008027799 A2 | 3/2008 |

OTHER PUBLICATIONS

International Search Report and Written Opinion (dated Nov. 30, 2015), International Application No. PCT/US2015/051325, International Filing date Sep. 22, 2015, Priority date Sep. 24, 2014, 6 pages.

*Primary Examiner* — Brian Gulledge
(74) *Attorney, Agent, or Firm* — Cantor Colburn LLP; Tina Dorr, Esq.; Ram W. Sabnis

(57) ABSTRACT

The present invention is directed to wet wipes and methods of making thereof. In one aspect, a wet wipe includes a multi-ply tissue impregnated with a wetting composition. The multi-ply tissue includes papermaking fibers, is substantially free of synthetic fibers, and has an absorbent capacity of at least about 8 grams of the wetting composition per gram of the dry multi-ply tissue (g/g) as measured in accordance with American Society for Testing and Materials International (ASTM International) standard D4250. A
(Continued)

single ply of the multi-ply tissue has a basis weight of at least 8 pounds per 3,000 square foot ream (lb/rm).

19 Claims, 4 Drawing Sheets

(51) Int. Cl.
*A47K 10/38* (2006.01)
*A61K 8/02* (2006.01)
*A61K 8/67* (2006.01)
*A61Q 19/00* (2006.01)
*B65D 85/671* (2006.01)
*D21H 11/04* (2006.01)
*D21H 11/12* (2006.01)
*D21H 21/20* (2006.01)
*D21H 27/30* (2006.01)
*A47K 10/32* (2006.01)

(52) U.S. Cl.
CPC .............. *A61K 8/678* (2013.01); *A61Q 19/00* (2013.01); *B65D 85/671* (2013.01); *D21H 11/04* (2013.01); *D21H 11/12* (2013.01); *D21H 21/20* (2013.01); *D21H 27/30* (2013.01); *A47K 2010/3266* (2013.01); *A61K 2800/10* (2013.01); *A61K 2800/56* (2013.01)

(56) References Cited

U.S. PATENT DOCUMENTS

2005/0090175 A1\* 4/2005 Bergholm .............. D04H 1/425
　　　　　　　　　　　　　　　　　　　　442/408
2009/0183846 A1\* 7/2009 Hermans ................. D21F 11/14
　　　　　　　　　　　　　　　　　　　　162/109
2009/0321027 A1　12/2009 Hermans et al.

\* cited by examiner

US 10,351,998 B2

PRE-MOISTENED WET WIPE PRODUCTS IN PERFORATED ROLL FORM MADE OF TISSUE BASED SUBSTRATES

TECHNICAL FIELD

The instant invention generally is related to wet wipes. More specifically, the instant invention is related multi-ply wet wipes.

BACKGROUND OF THE INVENTION

Conventional pre-moistened wet wipe substrates are made from synthetic fibers, such as rayon, polyester, or polypropylene, in a non-woven sheet. Synthetic materials have been used because of their high wet tensile strength and compatibility with wet wipe chemistry. However, the cost of these nonwoven synthetic substrates is presently about $3,000 to $4,000 per ton, which is due to the synthetic material costs involved and the non-woven production process.

In contrast, cellulose-based wipe substrates made of papermaking fibers are more cost effective and environmentally sustainable. Because a conventional paper machine has a much higher production rate than nonwoven machines, the current cost of virgin cellulose-based paper sheets may only be around $800 per ton. However, cellulose-based wipe substrates may have lower tensile strength and absorbent capacity compared to synthetic nonwoven substrates.

Thus, there still exists a need for a low-cost, high absorbance cellulose-based wet wipe. It is to solving this need the present invention is directed.

SUMMARY OF THE INVENTION

The present invention is directed to wet wipes and methods of making thereof. In one aspect, a wet wipe includes a multi-ply tissue impregnated with a wetting composition. The multi-ply tissue includes papermaking fibers, is substantially free of synthetic fibers, and has an absorbent capacity of at least about 8 grams of the wetting composition per gram of the dry multi-ply tissue (g/g) as measured in accordance with American Society for Testing and Materials International (ASTM International) standard D4250. A single ply of the multi-ply tissue has a basis weight of at least 8 pounds per 3,000 square foot ream (lb/rm).

In another aspect, a wet wipe includes a multi-ply tissue impregnated with a wetting composition. The multi-ply tissue includes papermaking fibers, is void of synthetic fibers, and has an absorbent capacity of at least about 8 grams of the wetting composition per gram of the dry multi-ply tissue (g/g) as measured in accordance with American Society for Testing and Materials International (ASTM International) standard D4250. A single ply of the multi-ply tissue has a basis weight of at least 8 pounds per 3,000 square foot ream (lb/rm).

Yet, in another aspect, a wet wipe includes a perforated multi-ply tissue impregnated with a wetting composition. The multi-ply tissue includes papermaking fibers, is void of synthetic fibers, and has an absorbent capacity of at least about 8 g/g as measured in accordance with ASTM International standard D4250. A single ply of the multi-ply tissue having a basis weight of at least about 8 lb/rm.

Still yet, in another aspect, a method of making a wet wipe includes forming a multi-ply tissue and impregnating the multi-ply tissue with a wetting composition to form the wet wipe. The multi-ply tissue includes papermaking fibers, is substantially free of synthetic fibers, and has an absorbent capacity of at least about 8 lb/rm as measured in accordance with ASTM International standard D4250.

It is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods, and systems for carrying out the present invention. It is important, therefore, that the claims be regarded as including such equivalent constructions insofar as they do not depart from the spirit and scope of the present invention.

Other advantages and capabilities of the invention will become apparent from the following description taken in conjunction with the examples showing aspects of the present invention.

BRIEF DESCRIPTION OF THE DRAWINGS

The invention will be better understood and the above object as well as other objects other than those set forth above will become apparent when consideration is given to the following detailed description thereof. Such description makes reference to the annexed drawing wherein.

DETAILED DESCRIPTION OF THE INVENTION

Figure 1:
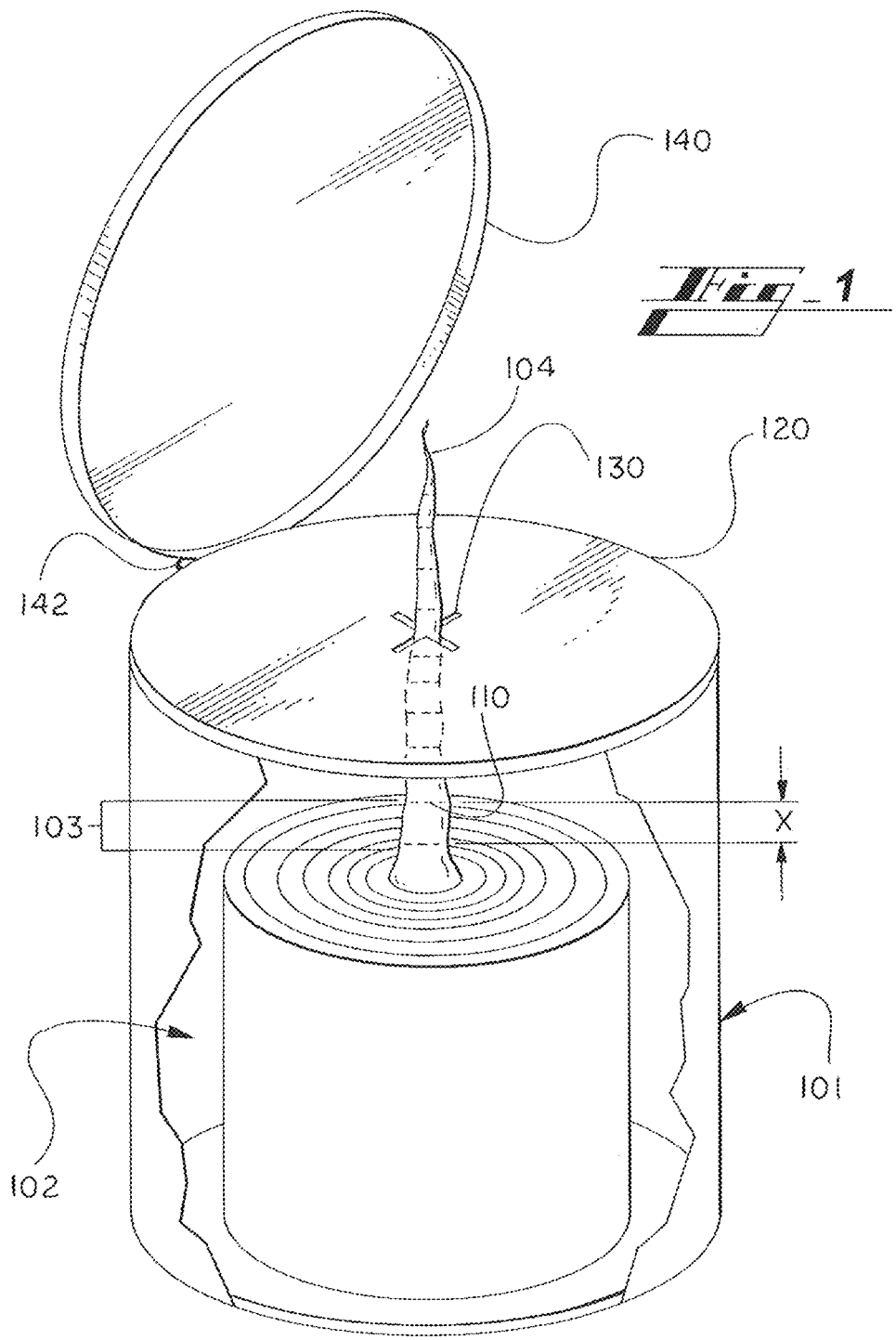
FIG. 1 is an illustration of a wet wipe roll in a dispenser having an orifice for accessing the wet wipe.

For a fuller understanding of the nature and desired objects of this invention, reference should be made to the above and following detailed description taken in connection with the accompanying figures. When reference is made to the figures, like reference numerals designate corresponding parts throughout the several figures.

The present invention is directed to wet wipes and methods of making thereof. In one aspect, a wet wipe includes a multi-ply tissue impregnated with a wetting composition. The multi-ply tissue includes papermaking fibers, is substantially free of synthetic fibers, and has an absorbent capacity of at least about 8 grams of the wetting composition per gram of the dry multi-ply tissue (g/g) as measured in accordance with American Society for Testing and Materials International (ASTM International) standard D4250. A single ply of the multi-ply tissue has a basis weight of at least 8 pounds per 3,000 square foot ream (lb/rm).

In another aspect, a wet wipe includes a multi-ply tissue impregnated with a wetting composition. The multi-ply tissue includes papermaking fibers, is void of synthetic fibers, and has an absorbent capacity of at least about 8 grams of the wetting composition per gram of the dry multi-ply tissue (g/g) as measured in accordance with American Society for Testing and Materials International (ASTM International) standard D4250. A single ply of the multi-ply tissue has a basis weight of at least 8 pounds per 3,000 square foot ream (lb/rm).

Yet, in another aspect, a wet wipe includes a perforated multi-ply tissue impregnated with a wetting composition. The multi-ply tissue includes papermaking fibers, is void of synthetic fibers, and has an absorbent capacity of at least about 8 g/g as measured in accordance with ASTM International standard D4250. A single ply of the multi-ply tissue having a basis weight of at least about 8 lb/rm.

Still yet, in another aspect, a method of making a wet wipe includes forming a multi-ply tissue and impregnating the multi-ply tissue with a wetting composition to form the wet wipe. The multi-ply tissue includes papermaking fibers, is substantially free of synthetic fibers, and has an absorbent capacity of at least about 8 lb/rm as measured in accordance with ASTM International standard D4250.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

As used herein, the articles "a" and "an" preceding an element or component are intended to be nonrestrictive regarding the number of instances (i.e. occurrences) of the element or component. Therefore, "a" or "an" should be read to include one or at least one, and the singular word form of the element or component also includes the plural unless the number is obviously meant to be singular.

As used herein, the terms "invention" or "present invention" are non-limiting terms and not intended to refer to any single aspect of the particular invention but encompass all possible aspects as described in the specification and the claims.

As used herein, the term "about" modifying the quantity of an ingredient, component, or reactant of the invention employed refers to variation in the numerical quantity that can occur, for example, through typical measuring and liquid handling procedures used for making concentrates or solutions in the real world. Furthermore, variation can occur from inadvertent error in measuring procedures, differences in the manufacture, source, or purity of the ingredients employed to make the compositions or carry out the methods, and the like. Whether or not modified by the term "about," the claims include equivalents to the quantities. In one aspect, the term "about" means within 10% of the reported numerical value, or within 5% of the reported numerical value.

As used herein, the terms "percent by weight," "% by weight," and "wt. %" mean the weight of a pure substance divided by the total dry weight of a compound or composition, multiplied by 100. Typically, "weight" is measured in grams (g). For example, a composition with a total weight of 100 grams, which includes 25 grams of substance A, will include substance A in 25% by weight.

Terminology used herein is given its ordinary meaning consistent with the exemplary definitions set forth immediately below; mils refers to thousandths of an inch; mg refers to milligrams and $m^2$ refers to square meters, percent means weight percent (dry basis), "ton" means short ton (2000 pounds) and so forth. Unless otherwise specified, the test specimens are prepared under standard Technical Association of the Pulp and Paper Industry (TAPPI) conditions; that is, conditioned in an atmosphere of 23°±1.0° C. (73.4°±1.8° F.) at 50% relative humidity for at least about 2 hours.

As used herein, the term "wet-wipes" refers to a cleansing wipe. The wet wipe may be used for cleansing the face, body, or other surface.

As used herein, the term "papermaking fiber(s)" means "cellulose fibers," "cellulosic fibers," or any fiber incorporating cellulose as a major constituent. Papermaking fibers include, but are not limited to, virgin pulp-derived fibers, recycled (secondary) cellulosic fibers, and fiber mixtures comprising reconstituted cellulosic fibers. Suitable papermaking fibers include, but are not limited to, non-wood fibers, such as cotton fibers or cotton derivative fibers, abaca fibers, kenaf fibers, sabai grass fibers, flax fibers, esparto grass fibers, straw fibers, jute hemp fibers, bagasse fibers, milkweed floss fibers, and pineapple leaf fibers; and wood fibers, such as those obtained from deciduous and coniferous trees, including softwood fibers, such as northern and southern softwood Kraft fibers; hardwood fibers, such as *eucalyptus* fibers, maple fibers, birch fibers, aspen fibers, or the like. Papermaking fibers include naturally occurring pulp-derived fibers, as well as reconstituted cellulosic fibers such as lyocell or rayon, to name only a few. Pulp-derived fibers are liberated from their source material by any one of a number of pulping processes familiar to one of ordinary skill in the art, including sulfate pulping, sulfite pulping, polysulfide pulping, soda pulping, etc. The pulp can be bleached by chemical means, including the use of chlorine, chlorine dioxide, oxygen, alkaline peroxide and so forth. Naturally occurring pulp-derived fibers are referred to herein simply as "pulp-derived" papermaking fibers. Further, as used herein, the term "synthetic fiber(s)" excludes reconstituted cellulose fibers, such as lyocell or rayon, to name only a few. In one aspect, reconstituted cellulose fibers can be employed in the invention.

In one aspect, the papermaking fibers are present in the multi-ply substrate in an amount in a range between about 95 and about 100 wt. %. In another aspect, the papermaking fibers are present in the multi-ply substrate in an amount in a range between about 99 and about 100 wt. %. Yet, in another aspect, the papermaking fibers are present in the multi-ply substrate in an amount in a range between about 96 and about 100 wt. %. Still yet, in another aspect, the papermaking fibers are present in the multi-ply substrate in an amount in a range between about 90 and about 100 wt. %. In one aspect, the papermaking fibers are present in the multi-ply substrate in an amount about or in any range between about 90, 91, 92, 93, 94, 95, 96, 97, 98, 99, and 100 wt. %.

As used herein, the term "synthetic fiber(s)" means fibers made of any man-made or synthetic material, such as a polymeric material. Polymeric materials include, but are not limited to, polyesters, polypropylehes, polyethylenes, polyethers, polyamides, polyhydroxyalkanoates, polysaccharides, or any combination thereof. Other non-limiting examples of polymeric materials include poly(ethylene terephthalate), poly(butylene terephthalate), poly(1,4-cyclohexylenedimethylene terephthalate), isophthalic acid copolymers (e.g., terephthalate cyclohexylene-dimethylene isophthalate copolymer), ethylene glycol copolymers (e.g., ethylene terephthalate cyclohexylene-dimethylene copolymer), polycaprolactone, poly(hydroxyl ether ester), poly(hydroxyl ether amide), polyesteramide, poly(lactic acid), polyhydroxybutyrate, and combinations thereof.

As used herein, the terms "basis weight," "BWT," "bwt," and so forth refer to the weight of a 3,000 square foot ($ft^2$) ream of tissue and is cited in units of pounds per ream (lb/rm). As used herein, the term "consistency" refers to percent solids of a nascent web, for example, calculated on a bone dry basis.

As used herein, the term "high strength tissue" or "HST" mean a tissue substrate including papermaking fibers and having a basis weight of at least about 8 lb/rm.

As used herein, the terms "caliper" or "bulk" refer to thickness of a tissue sheet. Caliper or bulk reported herein can be measured using 1, 4, or 8 sheet calipers as specified. The sheets are stacked, and the caliper measurements are taken at the central portion of the stack. Then the test samples may be measured with a Thwing-Albert Model 89-II-JR or Progage Electronic Thickness Tester, with 2-in (50.8 mm) diameter anvils, 539±10 grams dead weight load, and 0.231 in./sec descent rate. For finished product testing, each sheet of product to be tested must have the same number of plies as the product when sold. Caliper units herein are reported as mils/sheet.

The terms "furnish" and "tissue furnish" mean aqueous compositions including papermaking fibers, and optionally, wet strength resins, debonders, and the like, for making paper products.

As used herein, the terms "multi-ply tissue" or "multi-ply substrate" mean a tissue substrate of papermaking fibers having at least two plies. Thus, a multi-ply tissue can be, for example, a two-ply tissue, a three-ply tissue, or four-ply tissue. A multi-ply tissue may be created by folding a single ply tissue. In one aspect, multi-ply tissues of the present invention are substantially free of synthetic fibers. In another aspect, multi-ply tissues are void of synthetic fibers.

The terms "tissue" and "tissue paper" means a soft, absorbent paper including papermaking fibers. Single plies of tissues used in accordance with the present invention have high basis weights, for example, at least about 8 lb/rm. In one aspect, the basis weight of a single ply of the tissue is in a range between about 10 lb/rm and about 20 lb/gm. In another aspect, the basis weight of a single ply of the tissue is in a range between about 12 lb/gm and about 22 lb/rm. Still yet, in another aspect, the basis weight of a single ply of the tissue is about or in any range between about 8, 9, 10, 11, 12, 13, 14, 15, 16, 17, 18, 19, 20, 21, 22, 23, 24, and 25 lb/rm.

As used herein, the term "substantially free" when used in reference to synthetic fibers means amounts of synthetic fibers not in excess of 10% by weight of the papermaking fibers. In another aspect, "substantially free" when used in reference to synthetic fibers means amounts of synthetic fibers not in excess of 9% by wt. of the papermaking fibers. Yet, in another aspect, "substantially free" when used in reference to synthetic fibers means amounts of synthetic fibers not in excess of 8% by wt. of the papermaking fibers. Still, in another aspect, "substantially free" when used in reference to synthetic fibers means amounts of synthetic fibers not in excess of 7% by wt. of the papermaking fibers. In one aspect, "substantially free" when used in reference to synthetic fibers means amounts of synthetic fibers not in excess of 6% by wt. of the papermaking fibers. In another aspect, "substantially free" when used in reference to synthetic fibers means amounts of synthetic fibers not in excess of 5% by wt. of the papermaking fibers. Yet, in another aspect, "substantially free" when used in reference to synthetic fibers means amounts of synthetic fibers not in excess of 4% by wt. of the papermaking fibers. Still yet, in another aspect, "substantially free" when used in reference to synthetic fibers means amounts of synthetic fibers not in excess of 3% by wt. of the papermaking fibers. In one aspect, "substantially free" when used in reference to synthetic fibers means amounts of synthetic fibers not in excess of 2% by wt. of the papermaking fibers. In another aspect, "substantially free" when used in reference to synthetic fibers means amounts of synthetic fibers not in excess of 1% by wt. of the papermaking fibers.

As used herein, the term "absorbent capacity" refers to the tissue's ability to absorb a liquid and is cited in units of grams of a liquid or wetting composition per gram of the dry multi-ply tissue. Unless otherwise noted, absorbent capacity is measured in accordance with ASTM International standard D4250.

As used herein, the term "liquid release" refers to the amount of absorbed liquid released from a tissue substrate upon wiping a surface. The liquid release is measured by using the wet wipe over a 10 square foot ($ft^2$) area. An initial weight of the wet wipe is measured. Then the wet wipe is placed on a surface, moved back and forth in a zig-zag motion 6 times. Each movement should be over a dry surface covering a total of 5 $ft^2$. After 6 movements, the wipe is turned over and the process is repeated over the remaining 5 $ft^2$ area. The weight of the used wipe is then measured. The amount of liquid released (in grams) equals the initial weight minus the wipe after use.

As used herein, the term "liquid retention" means the ability of individual sheets of a perforated tissue roll to retain absorbed liquid while being held in a vertical or substantially vertical position, for example within a orifice of a dispenser. Unless otherwise noted, liquid retention of a perforated wet wipe roll is measured by wetting or loading perforated rolls of multi-ply tissue with a liquid wetting composition. Initially, the dry weights of the first and second wipes of the roll are measured. Then the wet wipe roll is disposed within a dispenser container having an orifice. The first wipe of the roll is engaged in a vertical or substantially vertical position within the orifice for 1.5 hours, unless otherwise noted. Then the wet weights of the first and second wipes are measured. The dry weight of each wipe is subtracted from the wet weight, which equals the liquid weight. Then the liquid weight of the first wipe is divided by the liquid weight of the second wipe and multiplied by 100. Thus, liquid retention of the first wet wipe in the roll is expressed as a percentage of the liquid retained in the second wet wipe.

As used herein, the term "orifice" means a hole, slit, or cross in a dispenser through which individual wipes of a perforated wet wipe roll can be engaged, torn, and dispensed.

As used herein, the term "wet opacity" refers to the transparency of a wet substrate. Wet opacity is measured by TAPPI test method TM-425 with a wet substrate.

As used herein, the term "wetting composition" means an aqueous-based composition, emulsion, or lotion optionally including, for example, skin care additives (e.g., moisturizers, fragrances, colorants, buffers, and the like) disinfectants, antibacterial agents, and the like.

As used herein, the term "perforated," "perforations" and the like terms when used to describe the wet wipe or tissue substrate refers to a series of "tabs" spaced apart by "holes," which connect individual sheets in a continuous roll of tissue substrate. Tearing along the perforations through the continuous sheet, for example when inside a dispenser, allows individual sheets to be removed from the continuous sheet roll and/or dispenser. The perforations may be along the machine direction or cross direction of the substrate. Perforations are created in the conversion process.

As used herein, the term "perforation strength" refers to the property of the tissue or wet wipe to resist breaking or tearing along the perforations. The "wet perforation strength" is measured by securing a wet perforated wipe in a force gauge, pulling on the adjoining wipe to break the perforation, and recording the peak force attained. The "dry perforation strength" is measured by securing a dry perforated wipe in a force gauge, pulling on the adjoining wipe to break the perforation, and recording the peak force attained. A non-limiting example of a force gauge is a Wagner FDIX Force One gauge, modified with a clamp attachment to enable grabbing a wipe.

High strength tissue (HST), prepared from papermaking fibers, being substantially free or void of synthetic fibers, and having a high basis weight, is a desirable substrate for use in wet wipes due to its relatively low cost. However, tissue substrates may have several drawbacks, including poor wet opacity, low liquid absorbent capacity, low perforation strength, and low liquid retention.

More specifically, single-ply HST does not have significant void space within its substrate. Thus, without being bound by theory, liquid is held weakly to the substrate surface. Thus gravity will cause the liquid to drain from the wipe surface when the wipe is positioned vertically within the orifice of a dispenser. Thus, low liquid delivery results from the first wipe engaged within the orifice of a dispenser.

In addition, a perforated single-ply wipe requires that the wipe is passed through the orifice of the dispenser to break the perforation. This "drag force" is typically on the order of 2.5 to 3 $lb_f$, which may tear the substrate in regions outside the perforations.

Finally, since HST is a thin material, the substrate may become transparent when wet. This transparency may be disfavored by consumers, who require a barrier to be present between their hand and the soil they are cleaning.

The multi-ply HST wet wipe product of the present disclosure addresses these shortcomings. In particular, adding at least another ply effectively doubles the opacity of the wet sheet. Without being bound by theory, it is believed that the additional ply also creates a void space between the sheets, allowing for stronger capillary action. Further, again without being bound by theory, it is believed that increasing the void space of the sheet thereby improves liquid absorption and retention. Further, the additional ply increases the bulk of the sheet, improving both dispensing through an orifice in a dispenser and hand feel during use.

Any method may be used to produce the multi-ply tissue. At least two plies may be used and combined to form the multi-ply tissue. For example, the multi-ply tissue may have two plies, three plies, or four plies. In one example, two single-ply tissue sheets are rewound into a 2-ply "child" roll. The "child" roll is then converted (rolled, embossed, and/or perforated) as a single-ply roll would be converted. The multi-ply tissue may be passed through an embossing nip to provide an embossed multi-ply tissue.

In another method of making a multi-ply tissue, a single-ply child roll that is folded in half during converting and rewound to form a 'pseudo' 2-ply tissue. This method has the advantage of lower cost (fewer processes involved). Additionally, in the event the plies come apart during use, the user will not be confronted with multiple sheets.

To manufacture the 'pseudo' 2-ply product, the roll is unwound and initially slit into 2 lanes. Each lane, for example, may have a width in a range between about 4 and about 18 inches. Each lane is then folded in half with the edges meeting in the middle. The two lanes are then slit in half again, creating four lanes wide. Further, the multi-ply tissue can be formed by folding a single ply of a tissue to combine opposite ends of the tissue. The sheet then passes through the perforator and is rewound into finished perforated rolls ("donuts"). Thus, the wet wipe can be wound into the form of a wet wipe roll.

The individual plies in the multi-ply tissue can be held together with or without an adhesive. Any suitable adhesive can be used. A non-limiting example of a suitable adhesive is polyvinyl alcohol. The plies can be attached by needling. In addition, the surface tension of wetting composition may keep the plies in contact with one another. In one aspect, no chemical bonding is required.

Upon forming the multi-ply tissue substrate, the substrate may be perforated to enable use within a container or dispenser. The perforations enable individual tissue sheets to be removed from the container or dispenser by pulling through the dispenser orifice and applying pressure at an angle to tear the sheet from the roll.

FIG. 11 illustrates an exemplary wet wipe roll 102 disposed within a dispenser 101 with an orifice 130 for accessing the wet wipe. The dispenser 101 may be any size or shape and may include a top 120 to cover the wet wipe roll 102 in the bottom of the dispenser 101. The dispenser 101 can also include a lid 140, optionally attached to the dispenser 101 by a hinge 142. The top 120 ensures that the wet wipe roll 120 remains moist, preventing evaporation from the orifice 130. The top 120 includes the orifice 130 that acts as a brake by controlling the tension on the wet wipe 104 as it is dispensed. The orifice 130 may be any shape or size, including but not limited to, a funnel or cross shape.

The wet wipe roll 102 may have perforations 110 to enable dispensing of individual sheets 103. The distance, x, between the perforation 110 lines determines the length of material dispensed. As the wet wipe 104 is pulled through the orifice 130 from the dispenser 101, it is forced through the orifice 130. The orifice 130 is sized such that the force applied by the user to remove the towel increases to an amount higher than the perforation strength of the towel or web material. Continued pulling causes the wet wipe 104 to break and provides the user with a single sheet.

The optimal perforation pattern (hole/tab width and spacing) is weak enough to allow acceptable dispensing, but strong enough to avoid breaks during converting. The optimal perforation pattern is determined by analyzing the wipe's wet and dry perforation strength, along with its drag through the orifice of the dispenser.

The perforation pattern is not intended to be limited and may be tailored based on the properties of the multi-ply tissue (e.g., number of plies and basis weight) and the dispenser orifice/closure. The perforation pattern includes "tabs" spaced apart by "holes." Although not intended to be limiting, the tabs may between about 0.005 to about 1 inch long. The tabs may be spaced apart, or the holes may be about, 0.05 to about 2 inches long. In one aspect, the tabs and holes may have variable lengths and spacing distances across the tissue substrate.

The perforation strength, both wet and dry, is substantially linearly proportional to the tab area in the perforation. For optimal dispensing, the perforation strength of the tissue should be less than the drag force through the dispenser closure/orifice. The drag force (in units of pounds of force, or $lb_f$) is measured by securing the end of a wipe to a force gauge, pulling the wipe through the closure/orifice, and measuring the peak force experienced during the pull.

To improve dispensing, the drag force through the orifice may be increased by modifying the dispenser orifice, e.g. making it narrower. The perforation strength also may be increased by altering the perforation pattern. The perforation tabs may have varying lengths, with larger tabs present on the substrate edges. Although tissue substrates require a high initial break force because of the inability to stretch or elongate, like substrates including synthetic fibers, much less force is required after an initial tear starts on one edge.

Individual plies of the multi-ply tissue can be prepared according to conventional processes known to those skilled in the art, including conventional wet pressing, through-air-drying (TAD), Yankee air drying, and variations thereof. The tissue substrates may be creped or un-creped.

For example, wet pressed tissues can be prepared by first preparing and mixing the raw papermaking fiber material with water and desired additional additives in a vat to produce a fiber slurry. Optionally, the fiber slurry includes a wet-strength resin, debonders, and/or other additives.

The wet strength resin can be temporary or permanent and may be any compound capable of increasing the wet strength of the tissue. Non-limiting examples of suitable wet strength resins include glyoxal; glutaraldehyde; uncharged chemical moieties, such as dialdehydes, aldehyde-containing polyols, uncharged aldehyde-containing polymers, and cyclic ureas and mixtures thereof, and aldehyde-containing cationic starch; mixtures of polyvinyl alcohol and salts of multivalent anions, such as boric acid or zirconium ammonium carbonates; glyoxalated polyacrylamide; polyamine-epihalohydrins, such as polyamine epichlorohydrin; polyamide epihalohydrins, such as polyamide epichlorohydrin; polyamide-amine epihalohydrins, such as polyamide-amine epichlorohydrin; ureaformaldehyde; melamine-formaldehyde; polyethyleneimine; or any combinations thereof.

In one aspect, the wet strength resin is present in a range between about 0.1 wt. % and about 5 wt. % based on the total weight of the papermaking fibers. In another aspect, the wet strength resin is present in a range between about 0.25 wt. % and about 2.5 wt. % based on the total weight of the papermaking fibers. Yet, in another aspect, the wet strength resin is present in an amount about or in any range between about 0.1, 0.3, 0.5, 0.7, 1.0, 1.3, 1.5, 1.7, 2.0, 2.3, 2.5, 2.7, 3.0, 3.3, 3.5, 3.7, 4.0, 4.3, 4.5, 4.7, and 5.0 wt. % based on the total weight of the papermaking fibers.

Optionally, the tissue fiber slurry includes a debonder, or a "softener." Debonders may be any compound(s) used to decreasing tensile strength or soften the tissue paper. Debonder compositions may include cationic or anionic amphiphilic compounds, or mixtures thereof (surfactants) combined with other diluents and non-ionic amphiphilic compounds. Diluents include, but are not limited to, propylene glycol, ethanol, propanol, water, polyethylene glycols, and nonionic amphiphilic compounds. Surfactants include quaternary ammonium compounds, such as dialkyl dimethyl quaternary ammonium salts, e.g. with alkyl groups containing from about 10 to 24 carbon atoms.

Biodegradable softeners may be utilized. Non-limiting examples of suitable biodegradable cationic softeners/debonders include biodegradable diesters of quaternary ammonia compounds, quaternized amine-esters, and biodegradable vegetable oil based esters functionalized with quaternary ammonium chloride and diester dierucyldimethyl ammonium chloride.

One method of making a single tissue ply involves diluting the fiber slurry to the desired consistency (e.g., between about 0.1% and about 1.0%) and transferring through a centrifugal pump to a headbox. From the headbox, the fibrous mixture is deposited onto a moving foraminous wire, such as fourdrinier wire, to form a nascent web. Water can drain through the wire by use of vacuum and/or drainage elements. For drying on a Yankee dryer, first an adhesive material (creping adhesive) is sprayed onto the surface of the Yankee dryer drum. The nascent web is transferred onto the hot Yankee dryer via one or two press rolls. The web is dried on the Yankee dryer and then removed with a creping doctor, which scrapes the web from the surface of the Yankee dryer drum.

Another drying method is TAD. In this method, the paper is dried by means of hot air blown through the moist paper web, often without a preceding wet pressing. In connection with the TAD drying, the patterned structure of the drying fabric is transferred to the paper web. This structure is also essentially maintained in the wet condition of the paper, since it has been imparted to the wet paper web.

Compared to single ply tissues, the multi-ply substrates of the present invention demonstrate a significant improvement in absorbent capacity, liquid delivery, liquid retention, and wet opacity. The multi-ply wet wipe product also provides a more consistent feel, avoiding the 'dripping wet' observation with the single-ply product. Finally, the multi-ply product provides improved dispensing due to the increased bulk of the sheet.

In one aspect, the absorbent capacity of the multi-ply substrate is at least about 8 g/g as measured in accordance with ASTM International standard D4250. In another aspect, the absorbent capacity of the multi-ply tissue is in a range between about 9 and about 11 g/g as measured in accordance with ASTM International standard D4250. Yet in another aspect, the absorbent capacity of the multi-ply tissue is in a range between about 8 and about 12 g/g as measured in accordance with ASTM International standard D4250. Still yet, in another aspect, the absorbent capacity of the multi-ply tissue is at least about or in any range between about 8, 9, 10, 11, 12, or 13 g/g as measured in accordance with ASTM International standard D4250.

One potential drawback to using conventional tissue substrates in a wet wipe roll is the wipes may lose liquid while remaining in an elevated position within the orifice of a dispenser. In particular, the first wet wipe within a roll (the wipe positioned within the orifice) may be drier than the second (and other successive wipes) because liquid may drain from the first wipe in the elevated position. Furthermore, when conventional tissue substrates are used as wet wipes, liquid may only absorb loosely onto the surface of the wipe. However, the inventive high strength multi-ply tissue provides for enhanced liquid retention of the first wipe by allowing a void space between the sheets to hold liquid. After being positioned in the orifice of a dispenser for 1.5 hours (described above), 74% of the liquid is retained in the first wipe of a perforated wet wipe roll compared to the second and successive wipes. This result compares to 47% retention for a single ply wet wipe. The improvement in liquid retention in the multi-ply perforated wet wipe product of the present invention is comparable to other commercially available substrates including synthetic fibers (e.g., SANI-HANDS ALC, available from Professional Disposables International, Inc., Orangeburg, N.Y., with 79% retention).

When a perforated multi-ply substrate roll of the present invention is wetted with a wetting composition, and the first wipe is engaged within a orifice of a dispenser for 1.5 hours, the liquid retained on the first wipe is in a range between about 50 and about 100% compared to the second wipe, which is not elevated. In another aspect, the liquid retention of first wipe is in a range between about 70 and about 90% compared to the second wipe. Yet in another aspect, the liquid retention of the first wipe is in a range between about 60 and about 95% compared to the second wipe. Still yet, in another aspect, the liquid retention of the first wipe is about or in any range between about 50, 55, 60, 65, 70, 75, 80, 85, 90, 95, and 100% compared to the second wipe.

Low absorbent capacity of conventional single ply tissues results in low amounts of liquid delivered when used by a user. The more liquid delivered, the more efficacious the wipe will be. When liquid release of the multi-ply substrate comprising papermaking fibers is assessed as described above, the amount of liquid released is at least about 0.5 g. In another aspect, the liquid release of the multi-ply substrate comprising papermaking fibers is at least about 1.0 g. Yet, in another aspect, the liquid release of the multi-ply substrate comprising papermaking fibers is at least about 1.5 g.

Reduction in opacity due to wetting may be a problem when the wipe substrate has a substantial amount of cellulosic fibers. Although substituting synthetic fibers for cellulosic fibers may improve wet opacity, substitution is undesirable from a cost standpoint.

However, as disclosed herein, adding at least a second tissue ply of a HST improves wet opacity. For example, compared to a single-ply HST having a wet opacity of about 24.3, a second ply provides a wet opacity of about 36.0, a significant improvement. In one aspect, the wet opacity of the multi-ply substrate is in a range between about 10 and about 90. In another aspect, the wet opacity of the multi-ply substrate is in a range between about 20 and about 80. Yet in another aspect, the wet opacity of the multi-ply substrate is in a range between about 30 and about 60. Still yet, in another aspect, the wet opacity of the multi-ply substrate is about or in any range between about 10, 15, 20, 25, 30, 35, 40, 45, 50, 55, 60, 65, 70, 75, 80, 85, and 90.

The wet wipe can be impregnated or pre-moistened with a wetting composition, which can include at least one additive. The wetting composition can be any solution, including, but not limited to, an aqueous solution comprising at least one additive. Non-limiting examples of suitable additives are provided below. The wetting composition can be disposed on or impregnated within the multi-ply tissue substrate by any method. Examples of such methods include, but are not limited to, soaking the multi-ply tissue in the wetting composition and spraying the wetting composition onto the multi-ply tissue.

The wetting composition can be added to the multi-ply tissue in any amount desired. In one aspect, the wetting composition is added to the multi-ply tissue in an amount 2.0×, 2.5×, or 3.0× the weight of the multi-ply tissue. In another aspect, the wetting composition is added to the multi-ply tissue in an amount at least 2.0× the weight of the multi-ply tissue. Yet in another aspect, the wetting composition is added to the multi-ply tissue in an amount about or in any range between about 1.0, 1.5, 2.0, 2.5, 3.0, 3.5, 4.0, 4.5, 5.0, 5.5, or 6.0× the weight of the multi-ply tissue.

As indicated above, a variety of additives can be added to the wetting composition. Suitable additives include, but are not limited to: skin-care additives; odor control agents; de-tackifying agents if a binder is present to reduce the tackiness of the binder; disinfectants; particulates; antimicrobial agents; preservatives; wetting agents and cleaning agents such as detergents, surfactants, and some silicones; emollients; surface feel modifiers for improved tactile sensation (e.g., lubricity) on the skin; fragrance; fragrance solubilizers; opacifiers; fluorescent whitening agents; UV absorbers; pharmaceuticals; and pH control agents, such as malic acid or potassium hydroxide.

Skin-care additives provide one or more benefits to the user, such as a reduction in the probability of having diaper rash and/or other skin damage caused by fecal enzymes. These enzymes, particularly trypsin, chymotrypsin and elastase, are proteolytic enzymes produced in the gastrointestinal tract to digest food. In infants, for example, the feces tend to be watery and contain, among other materials, bacteria, and some amounts of undegraded digestive enzymes. These enzymes, if they remain in contact with the skin for any appreciable period of time, may cause an irritation that is uncomfortable in itself and can predispose the skin to infection by microorganisms. As a countermeasure, skin-care additives include, but are not limited to, the enzyme inhibitors and sequestrants.

The wetting composition can contain less than about 5 weight percent of skin-care additives based on the total weight of the wetting composition. More specifically, the wetting composition can contain from about 0.01 weight percent to about 2 weight percent of skin-care additives. Even more specifically, the wetting composition can contain from about 0.01 weight percent to about 0.05 weight percent of skin-care additives.

A variety of skin-care additives can be added to the wetting composition and the pre-moistened wipes of the present invention or included therein. For example, skin-care additives in the form of particles can be added to serve as fecal enzyme inhibitors, offering potential benefits in the reduction of diaper rash and skin damage caused by fecal enzymes. Such materials can be used in the present invention, including reaction products of a long chain organic quaternary ammonium compound with one or more of the following clays: montmorillonite, bentonite, beidellite, hectorite, saponite, and stevensite.

Other known enzyme inhibitors and sequestrants can be used as skin-care additives in the wetting composition of the present invention, including those that inhibit trypsin and other digestive or fecal enzymes, and inhibitors for urease. For example, enzyme inhibitors and anti-microbial agents may be used to prevent the formation of odors in body fluids. Such inhibitors can be incorporated into the wetting composition and the pre-moistened wipes of the present invention and include transition metal ions and their soluble salts, such as silver, copper, zinc, ferric, and aluminum salts. The anion may also provide urease inhibition, such as borate, phytate, etc. Compounds of potential value include, but are not limited to, silver chlorate, silver nitrate, mercury acetate, mercury chloride, mercury nitrate, copper metaborate, copper bromate, copper bromide, copper chloride, copper dichromate, copper nitrate, copper salicylate, copper sulfate, zinc acetate, zinc borate, zinc phytate, zinc bromate, zinc bromide, zinc chlorate, zinc chloride, zinc sulfate, cadmium acetate, cadmium borate, cadmium bromide, cadmium chlorate, cadmium chloride, cadmium formate, cadmium iodate, cadmium iodide, cadmium permanganate, cadmium nitrate, cadmium sulfate, and gold chloride. Other salts known to have urease inhibition properties include ferric and aluminum salts, such as the nitrates, and bismuth salts. Other urease inhibitors include hydroxamic acid and its derivatives; thiourea; hydroxylamine; salts of phytic acid; extracts of plants of various species, including various tannins, e.g. carob tannin, and their derivatives such as chlorogenic acid derivatives; naturally occurring acids such as ascorbic acid, citric acid, and their salts; phenyl phosphoro diamidate/diamino phosphoric acid phenyl ester; metal aryl phosphoramidate complexes, including substituted phosphorodiamidate compounds; phosp oramidates without substitution on the nitrogen; boric acid and/or its salts, including especially, borax, and/or organic boron acid compounds; sodium, copper, manganese, and/or zinc dithiocarbamate; quinones; phenols; thiurams; substituted rhodanine acetic acids; alkylated benzoquinones; formamidine disulphide; 1:3-diketones maleic anhydride; succinamide; phthalic anhydride; pehenic acid; N,N-dihalo-2-imidazolidinones; N-halo-2-oxazolidinones; thio- and/or acyl-phosphoryltnamide and/or substituted derivatives thereof, thiopyridine-N-oxides, thiopyridines, and thiopyrimidines; oxidized sulfur derivatives of diarninophosphinyl compounds; cyclotriphosphazatriene derivatives; bromo-nitro compounds; S-aryl and/or alkyl diamidophosphorothiolates; diarninophosphinyl derivatives; mono- and/or polyphosphorodiamide; alkoxy-1,2-benzothaizin compounds; ortho-diaminophosphinyl derivatives of oximes; 5-substituted-benzoxathiol-2-ones; N(diammophosphinyl)arylcarboxamides; etc.

Many other skin-care additives may be incorporated into the wetting composition and pre-moistened wipes of the present invention, including, but not limited to, sun blocking agents and UV absorbers, acne treatments, pharmaceuticals, baking soda (including encapsulated forms thereof), vitamins and their derivatives such as Vitamins A or E, botanicals such as witch hazel extract and aloe vera, allantoin, emollients, disinfectants, hydroxy acids for wrinkle control or anti-aging effects, sunscreens, tanning promoters, skin lighteners, deodorants and anti-perspirants, ceramides for skin benefits and other uses, astringents, moisturizers, nail polish removers, insect repellants, antioxidants, antiseptics, anti-inflammatory agents and the like.

Suitable odor control additives for use in the wetting composition and pre-moistened wipes of the present invention include, but are not limited to, zinc salts; talc powder; encapsulated perfumes (including microcapsules, macrocapsules, and perfume encapsulated in liposomes, vessicles, or microemulsions); chelants, such as ethylenediamine tetraacetic acid; zeolites; activated silica, activated carbon granules or fibers; activated silica particulates; polycarboxylic acids, such as citric acid; cyclodextrins and cyclodextrin derivatives; chitosan or chitin and derivatives thereof; oxidizing agents; antimicrobial agents, including silver-loaded zeolites; triclosan; kieselguhr; and mixtures thereof. In addition to controlling odor from the body or body wastes, odor control strategies can also be employed to mask or control any odor of the treated substrate. Typically, the wetting composition contains less than about 5 weight percent of odor control additives based on the total weight of the wetting composition. In another aspect, the wetting composition contains from about 0.01 weight percent to about 2 weight percent of odor control additives. Yet, in another aspect, the wetting composition contains from about 0.03 weight percent to about 1 weight percent of odor control additives.

The wetting composition and/or pre-moistened wipes may include derivatized cyclodextrins, such as hydroxypropyl beta-cyclodextrin in solution, which remain on the skin after wiping and provide an odor-absorbing layer. In other embodiments, the odor source is removed or neutralized by application of an odor-control additive, exemplified by the action of a chelant that binds metal groups necessary for the function of many proteases and other enzymes that commonly produce an odor. Chelating the metal group interferes with the enzyme's action and decreases the risk of malodor in the product.

If a binder is employed in the tissue substrate, detackifying agents can be used in the wetting composition to reduce the tackiness of the binder. Suitable detackifiers include any substance known in the art to reduce tack between two adjacent fibrous sheets treated with an adhesive-like polymer or any substance capable of reducing the tacky feel of an adhesive-like polymer on the skin. Detackifiers can be applied as solid particles in dry form, as a suspension or as a slurry of particles. Deposition can be by spray, coating, electrostatic deposition, impingement, filtration (i.e., a pressure differential drives a particle-laden gas phase through the substrate, depositing particles by a filtration mechanism), and the like, and can be applied uniformly on one or more surfaces of the substrate or may be applied in a pattern (e.g., repeating or random patterns) over a portion of the surface or surfaces of the substrate. The detackifier can be present throughout the thickness of the substrate, but may be concentrated at one or both surfaces, and may be substantially only present on one or both surfaces of the substrate. Specific detackifiers include, but are not limited to, powders, such as talc powder, calcium carbonate, mica; starches, such as corn starch; lycopodium powder; mineral fillers, such as titanium dioxide; silica powder; alumina; metal oxides in general; baking powder; kieselguhr; and the like. Polymers and other additives having low surface energy may also be used, including a wide variety of fluorinated polymers, silicone additives, polyolefins and thermoplastics, waxes, debonding agents known in the paper industry including compounds having alkyl side chains such as those having 16 or more carbons, and the like. Compounds used as release agents for molds and candle making may also be considered, as well as, dry lubricants and fluorinated release agents.

The wetting composition of the present invention can be further modified by the addition of solid particulates or microparticulates. Suitable particulates include, but are not limited to, mica, silica, alumina, calcium carbonate, kaolin, talc, and zeolites. The particulates can be treated with stearic acid or other additives to enhance the attraction or bridging of the particulates to the binder system, if desired. Also, two-component microparticulate systems, commonly used as retention aids in the papermaking industry, can be used. Such two-component microparticulate systems generally comprise a colloidal particle phase, such as silica particles, and a water-soluble cationic polymer for bridging the particles to the fibers of the web to be formed. The presence of particulates in the wetting composition can serve one or more useful functions, such as (1) increasing the opacity of the pre-moistened wipes; (2) modifying the rheology or reducing the tackiness of the pre-moistened wipe; (3) improving the tactile properties of the wipe; or (4) delivering desired agents to the skin via a particulate carrier, such as a porous carrier or a microcapsule. Typically, the wetting composition contains less than about 25 weight percent of particulate based on the total weight of the wetting composition. In another aspect, the wetting composition contains from about 0.05 weight percent to about 10 weight percent of microparticulate. Yet, in another aspect, the wetting composition contains from about 0.1 weight percent to about 5 weight percent of microparticulate.

Microcapsules and other delivery vehicles can also be used in the wetting composition of the present invention to provide skin-care agents; medications; comfort promoting agents, such as *eucalyptus*; perfumes; skin care agents; odor control additives; vitamins; powders; and other additives to the skin of the user. For example, the wetting composition can contain up to about 25 weight percent of microcapsules or other delivery vehicles based on the total weight of the wetting composition. In another aspect, the wetting composition can contain from about 0.05 weight percent to about 10 weight percent of microcapsules or other delivery vehicles. Yet, in another aspect, the wetting composition can contain from about 0.2 weight percent to about 5.0 weight percent of microcapsules or other delivery vehicles.

Microcapsules and other delivery vehicles are well known in the art. For example, POLY-PORE® E200 (Chemdal Corp., Arlington Heights, Ill.), is a delivery agent comprising soft, hollow spheres that can contain an additive at over 10 times the weight of the delivery vehicle. Known additives reported to have been used with POLY-PORE® E200 include, but are not limited to, benzoyl peroxide, salicylic acid, retinol, retinyl palmitate, octyl methoxycinnamate, tocopherol, silicone compounds (DC 435), and mineral oil. Another delivery vehicle which can be employed with non-woven fabric is a sponge-like material marketed as POLY-PORE® L200, which is reported to have been used with silicone (DC 435) and mineral oil. Other known delivery systems include cyclodextrins and their derivatives, liposomes, polymeric sponges, and spray-dried starch. Additives present in microcapsules are isolated from the environment and the other agents in the wetting composition until the wipe is applied to the skin, whereupon the microcapsules break and deliver their load to the skin or other surfaces.

The wetting composition of the present invention can contain preservatives and/or anti-microbial agents. Several preservatives and/or anti-microbial agents useful in the present invention include, but are not limited to, Mackstat H 66 (available from Mcintyre Group, Chicago, Ill.), DMDM hydantoin (e.g., Glydant Plus™, Lonza, Inc., Fair Lawn, N.J.), iodopropynyl butylcarbamate, Kathon (Rohm and Hass, Philadelphia, Pa.), methylparaben, propylparaben, 2-bromo-2-nitropropane-1,3-diol, benzoic acid, and the like. Typically, the wetting composition contains less than about 2 weight percent on an active basis of preservatives and/or antimicrobial agents based on the total weight of the wetting composition. In another aspect, the wetting composition contains from about 0.01 weight percent to about 1 weight percent of preservatives and/or anti-microbial agents. Yet, in another aspect, the wetting composition contains from about 0.01 weight percent to about 0.5 weight percent of preservatives and/or anti-microbial agents.

A variety of wetting agents and/or cleaning agents can be used in the wetting composition of the present invention. Suitable wetting agents and/or cleaning agents include, but are not limited to, detergents and nonionic, amphoteric, and anionic surfactants, especially amino acid-based surfactants. Amino acid-based surfactant systems, such as those derived from amino acids L-glutamic acid and other natural fatty acids, offer pH compatibility to human skin and good cleansing power, while being relatively safe and providing improved tactile and moisturization properties compared to other anionic surfactants. One function of the surfactant is to improve wetting of the dry substrate with the wetting composition. Another function of the surfactant can be to disperse bathroom soils when the pre-moistened wipe contacts a soiled area and to enhance their absorption into the substrate. The surfactant can further assist in make-up removal, general personal cleansing, hard surface cleansing, odor control, and the like. One commercial example of an amino-acid based surfactant is acylglutamate, marketed under the Amisoft name by Ajinomoto Corp., Tokyo, Japan. Typically, the wetting composition contains less than about 3 weight percent of wetting agents and/or cleaning agents based on the total weight of the wetting composition. In another aspect, the wetting composition contains from about 0.01 weight percent to about 2 weight percent of wetting agents and/or cleaning agents. Yet, in another aspect, the wetting composition contains from about 0.1 weight percent to about 0.5 weight percent of wetting agents and/or cleaning agents.

In addition to amino-acid based surfactants, a wide variety of surfactants can be used in the present invention. Suitable non-ionic surfactants include, but are not limited to, the condensation products of ethylene oxide with a hydrophobic (oleophilic) polyoxyalkylene base formed by the condensation of propylene oxide with propylene glycol. The hydrophobic portion of these compounds desirably has a molecular weight sufficiently high so as to render it water-insoluble. The addition of polyoxyethylene moieties to this hydrophobic portion increases the water-solubility of the molecule as a whole, and the liquid character of the product is retained up to the point where the polyoxyethylene content is about 50% of the total weight of the condensation product. Examples of compounds of this type include commercially-available Pluronic surfactants (BASF Wyandotte Corp.), such as those in which the polyoxypropylene ether has a molecular weight of about 1500-3000 and the polyoxyethylene content is about 35-55% of the molecule by weight, i.e. Pluronic L-62.

Other useful nonionic surfactants include, but are not limited to, the condensation products of $C_8$-$C_{22}$ alkyl alcohols with 2-50 moles of ethylene oxide per mole of alcohol. Other nonionic surfactants, which can be employed in the wetting composition of the present invention, include the ethylene oxide esters of $C_6$-$C_{12}$ alkyl phenols such as (nonylphenoxy)polyoxyethylene ether. Particularly useful are the esters prepared by condensing about 8-12 moles of ethylene oxide with nonylphenol, i.e. the IGEPAL® CO series (GAF Corp.). Further non-ionic surface active agents include, but are not limited to, alkyl polyglycosides (APG), derived as a condensation product of dextrose (D-glucose) and a straight or branched chain alcohol. The glycoside portion of the surfactant provides a hydrophile having high hydroxyl density, which enhances water solubility. Additionally, the inherent stability of the acetal linkage of the glycoside provides chemical stability in alkaline systems. Furthermore, unlike some non-ionic surface active agents, alkyl polyglycosides have no cloud point, allowing one to formulate without a hydrotrope, and these are very mild, as well as readily biodegradable non-ionic surfactants. This class of surfactants is available from Horizon Chemical under the trade names of APG-300, APG-350, APG-500, and APG-500.

Silicones are another class of wetting agents available in pure form, or as microemulsions, macroemulsions, and the like. One exemplary non-ionic surfactant group is the silicone-glycol copolymers. These surfactants are prepared by adding poly(lower)alkylenoxy chains to the free hydroxyl groups of dimethylpolysiloxanols and are available from the Dow Corning Corp as Dow Corning 190 and 193 surfactants (CTFA name: dimethicone copolyol). These surfactants function, with or without any volatile silicones used as solvents, to control foaming produced by the other surfactants, and also impart a shine to metallic, ceramic, and glass surfaces.

Anionic surfactants can be used in the wetting compositions of the present invention. Anionic surfactants are useful due to their high detergency include anionic detergent salts having alkyl substituents of 8 to 22 carbon atoms such as the water-soluble higher fatty acid alkali metal soaps, e.g., sodium myristate and sodium palmitate. A class of anionic surfactants which can be employed in the invention include, but are not limited to, the water-soluble sulfated and sulfonated anionic alkali metal and alkaline earth metal detergent salts containing a hydrophobic higher alkyl moiety (typically containing from about 8 to 22 carbon atoms) such as salts of higher alkyl mono or polynuclear aryl sulfonates having from about 1 to 16 carbon atoms in the alkyl group, with examples available as the Bio-Soft series, i.e. Bio-Soft D-40 (Stepan Chemical Co.).

Other classes of anionic surfactants which can be used with the invention include, but are not limited to, the alkali metal salts of alkyl naphthalene sulfonic acids (methyl naphthalene sodium sulfonate, Petro AA, Petrochemical Corporation); sulfated higher fatty acid monoglycerides such as the sodium salt of the sulfated monoglyceride of cocoa oil fatty acids and the potassium salt of the sulfated monoglyceride of tallow fatty acids; alkali metal salts of sulfated fatty alcohols containing from about 10 to 18 carbon atoms (e.g., sodium lauryl sulfate and sodium stearyl sulfate); sodium $C_{14}$-$C_{16}$-alphaolefin sulfonates such as the Bio-Terge series (Stepan Chemical Co.); alkali metal salts of sulfated ethyleneoxy fatty alcohols (the sodium or ammonium sulfates of the condensation products of about 3 moles of ethylene oxide with a $C_{12}$-$C_{15}$ n-alkanol, i.e., the Neodol ethoxysulfates, Shell Chemical Co.); alkali metal salts of higher fatty esters of low molecular weight alkylol sulfonic acids, e.g. fatty acid esters of the sodium salt of isothionic acid, the fatty ethanolamide sulfates; the fatty acid amides of amino alkyl sulfonic acids, e.g. lauric acid amide of taurine; as well as numerous other anionic organic surface active agents such as sodium xylene sulfonate, sodium naphthalene sulfonate, sodium toulene sulfonate and mixtures thereof.

A further useful class of anionic surfactants includes the 8-(4-n-alkyl-2-cyclohexenyl)-octanoic acids, wherein the cyclohexenyl ring is substituted with an additional carboxylic acid group. These compounds or their potassium salts, are commercially-available from Westvaco Corporation as Diacid 1550 or H-240. In general, these anionic surface active agents can be employed in the form of their alkali metal salts, ammonium or alkaline earth metal salts.

The wetting composition can further comprise an aqueous microemulsion of silicone particles, for example, organopolysiloxanes in an aqueous microemulsion. Typically, the wetting composition contains less than about 5 weight percent of a microemulsion of silicone particles based on the total weight of the wetting composition. In another aspect, the wetting composition contains from about 0.02 weight percent to about 3 weight percent of a microemulsion of silicone particles. Yet, in another aspect, the wetting composition contains from about 0.02 weight percent to about 0.5 weight percent of a microemulsion of silicone particles.

Silicone emulsions in general can be applied to the pre-moistened wipe by any known coating method. For example, the pre-moistened wipe may be moistened with a wetting composition comprising a water-dispersible or water-miscible, silicone-based component. Further, the wipe can comprise a nonwoven web of fibers having a water-dispersible binder, wherein the web is moistened with a lotion comprising a silicone-based sulfosuccinate. The silicone-based sulfosuccinate provides gentle and effective cleansing without a high level of surfactant. Additionally, the silicone-based sulfosuccinate provides a solubilization function, which prevents precipitation of oil-soluble components, such as fragrance components, vitamin extracts, plant extracts, and essential oils.

In one aspect of the present invention, the wetting composition comprises a silicone copolyol sulfosuccinate, such as disodium dimethicone copolyol sulfosuccinate and diammonium dimethicone copolyolsulfosuccinate. In one aspect, the wetting composition comprises less than about 2 percent by weight of the silicone-based sulfosuccinate, and, in another aspect, from about 0.05 percent to about 0.30 percent by weight of the silicone-based sulfosuccinate.

In another example of a product comprising silicone emulsion, Dow Corning 9506 powder can be present in the wetting composition. Dow Corning 9506 powder is believed to comprise a dimethicone/vinyldimethicone cross-polymer and is a spherical powder, which is said to be useful in controlling skin oils. Thus, a water-dispersible wipe, which delivers a powder effective in controlling skin oil, is also within the scope of the present invention.

The wetting composition of the present invention can contain one or more emollients. Suitable emollients include, but are not limited to, PEG 75 lanolin, methyl gluceth 20 benzoate, $C_{12}$-$C_{15}$ alkyl benzoate, ethoxylated cetyl stearyl alcohol, products marketed as Lambent wax WS-L, Lambent WD-F, Cetiol HE (Henkel Corp.), Glucam P20 (Amerchol), Polyox WSR N-10 (Union Carbide), Polyox WSR N-3000 (Union Carbide), Luviquat (BASF), Finsolv SLB 101 (Finetex Corp.), mink oil, allantoin, stearyl alcohol, Estol 1517 (Unichema), and Finsolv SLB 201 (Finetex Corp.).

An emollient can also be applied to a surface of the tissue substrate prior to or after wetting with the wetting composition. Such an emollient can be insoluble in the wetting composition and can be immobile except when exposed to a force. For example, a petrolatum-based emollient can be applied to one surface in a pattern, after which the other surface is wetted to saturate the wipe. Such a product could provide a cleaning surface and an opposing skin treatment surface.

The emollient composition in such products and other products of the present invention can comprise a plastic or fluid emollient such as one or more liquid hydrocarbons (e.g., petrolatum), mineral oil and the like, vegetable and animal fats (e.g., lanolin, phospholipids and their derivatives) and/or a silicone materials such as one or more alkyl substituted polysiloxane polymers, including the polysiloxane emollients. Optionally, a hydrophilic surfactant can be combined with a plastic emollient to improve wettability of the coated surface. Liquid hydrocarbon emollients and/or alkyl substituted polysiloxane polymers may be blended or combined with one or more fatty acid ester emollients derived from fatty acids or fatty alcohols.

The emollient material may be in the form of an emollient blend. For example, the emollient blend can comprise a combination of one or more liquid hydrocarbons (e.g., petrolatum), mineral oil and the like, vegetable and animal fats (e.g., lanolin, phospholipids and their derivatives), with a silicone material such as one or more alkyl substituted polysiloxane polymers. In another aspect, the emollient blend comprises a combination of liquid hydrocarbons (e.g., petrolatum) with dimethicone or with dimethicone and other alkyl substituted polysiloxane polymers.

Water-soluble, self-emulsifying emollient oils, which can be used in the present wetting compositions, include the polyoxyalkoxylated lanolins and the polyoxyalkoxylated fatty alcohols. The polyoxyalkoxy chains comprise mixed propylenoxy and ethyleneoxy units. The lanolin derivatives typically comprise about 20-70 such lower-alkoxy units while the $C_{12}$-$C_{20}$-fatty alcohols will be derivatized with about 8-15 lower-alkyl units. A non-limiting example of such a lanolin derivative is Lanexol AWS (PPG-12-PEG-50, Croda, Inc., New York, N.Y.). A non-limiting example of a poly(15-20)$C_2$-$C_3$-alkoxylate is PPG-5-Ceteth-20, known as Procetyl AWS (Croda, Inc.).

The wetting composition can include less than about 25 weight percent of emollients based on the total weight of the wetting composition. In another aspect, the wetting composition can comprise less than about 5 weight percent emollient, and, in yet another aspect, less than about 2% emollient. Still, in another aspect, the wetting composition can contain from about 0.01 weight percent to about 8 weight percent of emollients. Yet still, in another aspect, the wetting composition can contain from about 0.2 weight percent to about 2 weight percent of emollients.

In one aspect, the wetting composition and/or pre-moistened wipes of the present invention comprise an oil-in-water emulsion comprising an oil phase containing at least one emollient oil and at least one emollient wax stabilizer dispersed in an aqueous phase comprising at least one polyhydric alcohol emollient and at least one organic water-soluble detergent.

Surface-feel modifiers can be employed with the multi-ply tissue of the present invention to improve the tactile sensation (e.g., lubricity) of the skin during use of the product. Suitable surface feel modifiers include, but are not limited to, commercial debonders; and softeners, such as the softeners used in the art of tissue making including quaternary ammonium compounds with fatty acid side groups, silicones, waxes, and the like. Typically, the wetting composition contains less than about 2 weight percent of surface feel modifiers based on the total weight of the wetting composition. In another aspect, the wetting composition contains from about 0.01 weight percent to about 1 weight percent of surface feel modifiers. Yet, in another aspect, the wetting composition contains from about 0.01 weight percent to about 0.05 weight percent of surface feel modifiers.

A variety of fragrances can be used in the wetting composition of the present invention. Typically, the wetting composition contains less than about 2 weight percent of fragrances based on the total weight of the wetting composition. In another aspect, the wetting composition contains from about 0.01 weight percent to about 1 weight percent of fragrances. Yet, in another aspect, the wetting composition contains from about 0.01 weight percent to about 0.05 weight percent of fragrances.

Further, a variety of fragrance solubilizers can be used in the wetting composition of the present invention. Suitable fragrance solubilizers include, but are not limited to, polysorbate 20, propylene glycol, ethanol, isopropanol, diethylene glycol monoethyl ether, dipropylene glycol, diethyl phthalate, triethyl citrate, Ameroxol OE-2 (Amerchol Corp.), Brij 78 and Brij 98 (ICI Surfactants), Arlasolve 200 (ICI Surfactants), Calfax 16L-35 (Pilot Chemical Co.), Capmul POE-S(Abitec Corp.), Finsolv SUBSTANTIAL (Finetex), and the like. Typically, the wetting composition contains less than about 2 weight percent of fragrance solubilizers based on the total weight of the wetting composition. In another aspect, the wetting composition contains from about 0.01 weight percent to about 1 weight percent of fragrance solubilizers. Yet, in another aspect, the wetting composition contains from about 0.01 weight percent to about 0.05 weight percent of fragrance solubilizers.

Opacifers can be employed in the wetting composition. Suitable opacifiers include, but are not limited to, titanium dioxide or other minerals or pigments, and synthetic opacifiers such as REACTOPAQUE® particles (available from Sequa Chemicals, Inc., Chester, S.C.). Typically, the wetting composition contains less than about 2 weight percent of opacifiers based on the total weight of the wetting composition. In another aspect, the wetting composition contains from about 0.01 weight percent to about 1 weight percent of opacifiers. Yet, in another aspect, the wetting composition contains from about 0.01 weight percent to about 0.05 weight percent of opacifiers.

Suitable pH control agents for use in the wetting composition of the present invention include, but are not limited to, malic acid, citric acid, hydrochloric acid, acetic acid, sodium hydroxide, potassium hydroxide, and the like. An appropriate pH range minimizes the amount of skin irritation resulting from the wetting composition on the skin. Typically, the pH range of the wetting composition is from about 3.5 to about 6.5. In another aspect, the pH range of the wetting composition is from about 4 to about 6. Sill, in another aspect, the wetting composition contains less than about 2 weight percent of a pH adjuster based on the total weight of the wetting composition. In another aspect, the wetting composition contains from about 0.01 weight percent to about 1 weight percent of a pH adjuster. Yet, in another aspect, the wetting composition contains from about 0.01 weight percent to about 0.05 weight percent of a pH adjuster.

A variety of wetting compositions, formed from one or more of the above-described components, can be used with the wet wipes of the present invention.

EXAMPLES

Example 1

Wet wipes were prepared using wood pulp-based substrates made with virgin fibers. Each substrate ply had an average basis weight of about 12 to about 18 lb/3,000 ft$^2$. As shown in Table 1 below, an increased basis weight correlated with an increased wet tensile strength.

TABLE 1

Wet wipe basis weight compared to tensile strength

| Sample | | Caliper 8 Sheet mils/8 sheet | Basis Weight lb/3000 ft$^2$ | Tensite MD g/3 in | Stretch MD % | Tensile CD g/3 in | Stretch CD % | Tensile GM g/3 in. | Wet Tens Finch Cured-CD g/3 in. |
|---|---|---|---|---|---|---|---|---|---|
| 1-1 | 4910-1 04/29 | 37.43 | 12.86 | 2526 | 28.9 | 1532 | 5.2 | 1967 | 360.64 |
| 2-1 | 4910-2 | 39.40 | 14.27 | 3194 | 28.7 | 1874 | 4.8 | 2445 | 465.17 |
| 3-1 | 4910-3 | 40.55 | 15.14 | 3664 | 29.2 | 2197 | 4.3 | 2833 | 523.95 |
| 4-1 | 4910-4 | 45.88 | 18.70 | 4650 | 28.2 | 3630 | 3.9 | 4103 | 879.27 |
| 5-1 | 4910-5 | 46.05 | 17.71 | 4428 | 28.3 | 3009 | 4.2 | 3646 | 757.47 |
| 6-1 | 4910-6 | 47.13 | 18.46 | 4787 | 29.5 | 3228 | 4.0 | 3926 | 816.94 |
| 7-1 | 4910-7 | 45.83 | 18.25 | 4697 | 28.8 | 2679 | 4.4 | 3535 | 789.02 |

Example 2

The break modulus, tensile dry ratio, tensile total dry, and tensile energy absorption (T.E.A.) for the wet wipes of Example 1 are shown in Table 2. As shown, a higher basis weight tissue provided increased tensile, break modulus, and T.E.A.

TABLE 2

Properties of wet wipes compared to basis weight

| Sample | | Break Modules GM gms/% | Tensile Dry Ratio Unitless | Tensile Total Dry g/3 in | Basis Weight Raw Wt g | T.E.A. CD mm-gm/mm$^2$ | T.E.A. MD mm-gm/mm$^2$ |
|---|---|---|---|---|---|---|---|
| 1-1 | 4910-1 04/ | 162.98 | 1.65 | 4059 | 0.972 | 0.598 | 3.956 |
| 2-1 | 4910-2 | 199.99 | 1.72 | 5068 | 1.079 | 0.676 | 4.575 |
| 3-1 | 4910-3 | 242.76 | 1.68 | 5861 | 1.144 | 0.708 | 5.312 |
| 4-1 | 4910-4 | 395.67 | 1.29 | 8280 | 1.414 | 1.002 | 6.337 |
| 5-1 | 4910-5 | 344.45 | 1.48 | 7438 | 1.339 | 0.915 | 5.981 |
| 6-1 | 4910-6 | 375.40 | 1.50 | 8014 | 1.396 | 0.920 | 6.739 |
| 7-1 | 4910-7 | 310.85 | 1.79 | 7376 | 1.380 | 0.847 | 6.333 |

Example 3

Various wipe substrates were tested for the ability to maintain absorbed liquid when the wet wipe is elevated within the orifice of a dispenser (see FIG. 1). A perforated wet wipe roll was threaded through a canister orifice, and then individual wipes were dispensed and discarded.

Within each roll, the first wipe was engaged within the orifice of the dispenser, with about ¼ inch exposed. The canister was allowed to sit for two hours with the lid closed. After two hours, the first wipe was dispensed and weighed (initial weight). The wipe was then wiped across a surface with 6 back and forth motions and then weighed ("dry" weight). The second wipe was then dispensed, weighed, wiped across a surface, and re-weighed. The procedure was repeated for each wipe substrate.

Figure 2:
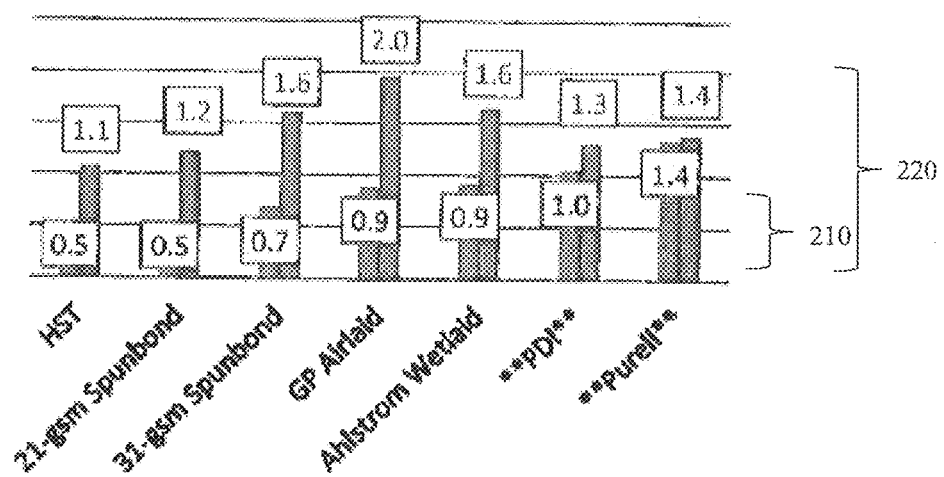
FIG. 2 is graph comparing liquid loss of various substrates when a wet wipe roll is elevated in the orifice of FIG. 1.

Various substrates were tested for liquid delivered per wipe (comparing the first and second wipes). As shown in FIG. 2, the high strength tissue (HST) and 21- and 31-grams per square meter (gsm) spunbond substrates lost nearly 50% of their liquid, compared to the second wipe 220, when the first wipe 210 was allowed to sit in an elevated position within the canister. In addition, both substrates deliver only about 0.5 to-0.7 g of liquid, which is substantially less than either the PDI substrate (a multi-bonded airlaid nonwoven, available from Contact PDI, Inc., Orangeburg, N.Y., SKU H776P134722) or the Purell substrate (a melt-blown nonwoven, available from Gojo Industries, Inc., Akron, Ohio, UPC No. 7385201747).

Example 4

Using a perforated, dry substrate roll, 2 sheets (plies) of HST were combined to form a 2-ply sheet (laying 1 on top of the other). Liquid was added to the sheets (an amount about 3 times the dry weight). The 2-ply sheet roll was tested for the ability to maintain absorbed liquid when elevated within an orifice within the dispenser as described in Example 3.

The initial dry and wet weights of the HST substrate were recorded. A single-ply HST substrate was also repeated as in Example 3 for comparison. The amount of liquid that was "lost" or drained from the substrate elevated in the orifice was calculated. The amount of liquid delivered to the surface after wiping was also calculated (see Table 3).

TABLE 3

Liquid retained in single and multi-ply substrates

| Sample | # ply | Dry weight | Wet weight | 2-Hour Weight | After wipe weight |
|---|---|---|---|---|---|
| 1 | 2 | 1.72 | 6.3 | 4.62 | 3.53 |
| 2 | 2 | 1.71 | 6.37 | 4.75 | 3.60 |
| 3 | 2 | 1.65 | 5.96 | 4.75 | 3.54 |
| 4 | 1 | 0.84 | 3.09 | 2.00 | 1.47 |
| 5 | 1 | 0.85 | 3.25 | 2.10 | 1.50 |
| 6 | 1 | 0.88 | 3.31 | 2.09 | 1.45 |

As shown in Table 4 below, use of a 2-ply wipe reduced the amount of liquid lost, or drained, from 49% to 33%. For comparison, the PDI control in Example 2 had a 30% loss.

TABLE 4

Amount of liquid lost and delivered

| Ply | % Liquid "lost" | Amount liquid delivered |
|---|---|---|
| 1 | 49% | 0.59 g |
| 2 | 33% | 1.15 g |

As also shown in Table 4, the amount of liquid delivered was improved. A 1-ply wipe delivered 0.59 g, while a 2-ply wipe delivered 1.15 g. These results indicate that liquid is not released as readily from a 2-ply wipe. More liquid may be held in between the sheets, which may be beneficial because the wipe will stay wet for a longer period of time.

Example 5

Perforated rolls "donuts" of 2-ply HST substrates (250-count) were wetted with varying levels of liquid (Table 5) (2.0×, 2.5×, and 3.0×) to determine liquid capacity. The liquid composition is shown in Table 6.

An empty canister was weighed and the weight was recorded. The scale was tared and a dry donut was added. The required amount of liquid (2.0×, 2.5×, or 3.0×) was calculated based on the weight of the dry donut. The required amount of liquid was added. The canister was closed and allowed to sit undisturbed for 3 days. The wet donut was removed from the canister (the donut was not frozen to avoid expelling additional liquid). The 'empty' canister was weighed to determine the amount of liquid that did not absorb. Experiments were performed duplicate. As shown in Table 5 below, the donut was unable to absorb liquid above a 2.0× loading ratio (this ratio was used in all subsequent examples).

TABLE 5

Ability to absorb liquid

| Loading Ration | Liquid Added (g) | Liquid Remaining in Canister (g) |
|---|---|---|
| 2.0x | 710 | 18.9, 21.2 |
| 2.5x | 880 | 132.4, 131.7 |
| 3.0x | 1060 | 262.6, 305.6 |

TABLE 6

Liquid composition

| Deionized Water | 27.3% |
|---|---|
| Ethyl Alcohol | 64.0% |
| Vitamin E Acetate | 0.1% |
| Isopropyl Alcohol | 1.5% |
| Glycerin | 3.5% |
| PEG-12 Dimethicone | 2.0% |
| Isopropyl Myristate | 1.0% |
| Propylene Glycol | 0.5% |

Example 6

The amount of liquid released in a roll of 2-ply HST substrate (250-count) was assessed. The liquid composition was the same as used in Table 6. In order to provide micro-efficiency, each wipe needed to deliver at least 1.0 g of liquid. The more liquid delivered, the more efficacious the wipe would be. N=5 replicates were performed.

As shown in Table 7, an average of 1.37 g of liquid was delivered per test design. In comparison, SANIHANDS ALC (available from Professional Disposables International, Inc., Orangeburg, N.Y.) delivered 1.6 g liquid using this method.

TABLE 7

Liquid released

| Replicate | Before wt (g) | After wt (g) | Liquid Released (g) |
|---|---|---|---|
| 1 | 3.68 | 2.33 | 1.35 |
| 2 | 3.73 | 2.41 | 1.32 |
| 3 | 3.80 | 2.43 | 1.37 |
| 4 | 4.06 | 2.51 | 1.55 |
| 5 | 3.79 | 2.55 | 1.24 |
| Average | | | 1.37 |

Example 7

One possible problem with single-ply HST is that the first wipe used (after the product hadn't been used for a while) may be excessively dry. For example, a 15 minute interval between uses resulted in the first wipe losing about 50% of its liquid. Thus, the first wipe used felt feel very dry, requiring a second wipe. The second wipe then seemed very saturated. The reason for this observation is that the liquid is unable to absorb into the substrate. Instead, the liquid adsorbs loosely onto the surface of the wipe. When the wipe is elevated, the liquid 'drains' back down into the canister. However, without being bound by theory, it is believed that the multi-ply product solved this problem by providing a void space between the sheets to hold the liquid and reduce this affect.

Five replicates were tested for the ability of a perforated HST substrate roll to retain liquid ("liquid retention"). The average data are shown below in Table 8. 250-count, 2-ply HST perforated (250 sheets) donuts were loaded with liquid (2.0× as shown in Table 5). The experiments were conducted within a dispenser with an orifice as described for Example 3, with the following exceptions. Initially, the wipes were not dispensed through the orifice. In step 1, 3 wipes were removed and individually weighed. The next wipe ("1$^{st}$ wipe") was allowed to remain elevated in the orifice. In step 2, the elevated wipe was removed and weighed after 1.5 hours. Steps 1 and 2 were repeated for the 2$^{nd}$, 3$^{rd}$, and 4$^{th}$ wipes.

TABLE 8

Wipe-to-wipe liquid retention

| Wipe Position | Wet Wipe Weight (g) | Dry Wipe Wt (g) | Liquid wt (g) |
|---|---|---|---|
| 1$^{st}$ Wipe | 3.3 | 1.5 | 1.8 |
| 2$^{nd}$, 3$^{rd}$, 4$^{th}$ | 3.9 | 1.5 | 2.4 |
| % Retention | | | 74% |

As shown in Table 8, 74% of the liquid was retained in the first wipe with the 2-ply product. This result compared to the 47% retention for the single ply product (data not shown). This result was a dramatic improvement and was comparable to other commercially available substrates including synthetic fibers (e.g., SANIHANDS ALC with a 79% retention).

Example 8

Absorbent capacity was measured for 1 and 2-ply HST substrates (Table 9). Absorbent capacity was measured in accordance with ASTM standard test method D4250.

TABLE 9

Absorbent capacity

| Number of plies | Basis Weight lb/3000 ft$^2$ (lb./rm) | Dry weight g | Wet weight g | Absorbent capacity g/g | Tensile CD g/3 in | Stretch CD % | T.E.A. CD mm-gm/mm$^2$ | Tensile MD g/3 in | Stretch MD % | T.E.A. MD mm-gm/mm$^2$ |
|---|---|---|---|---|---|---|---|---|---|---|
| 1 | 11.92 | 0.11 | 1.19 | 9.54 | 1508 | 5.1 | 0.588 | 3425 | 11.8 | 2.652 |
| 2 | 26.34 | 0.12 | 1.33 | 10.32 | 3363 | 4.9 | 1.265 | 6504 | 14.7 | 5.556 |
| 1 | 9 | 0.155 | 1.187 | 6.683 | — | — | — | — | — | — |
| 2 | 18 | 0.322 | 2.172 | 5.746 | — | — | — | — | — | — |

Example 9

An important property of a canister wipe is its perforation pattern. The optimum perforation pattern is weak enough to allow acceptable dispensing, yet strong enough to avoid breakouts during converting. This optimal perforation pattern may be identified by analyzing the wipe's wet and dry perforation strength, along with its drag through the closure/orifice.

Figure 3:
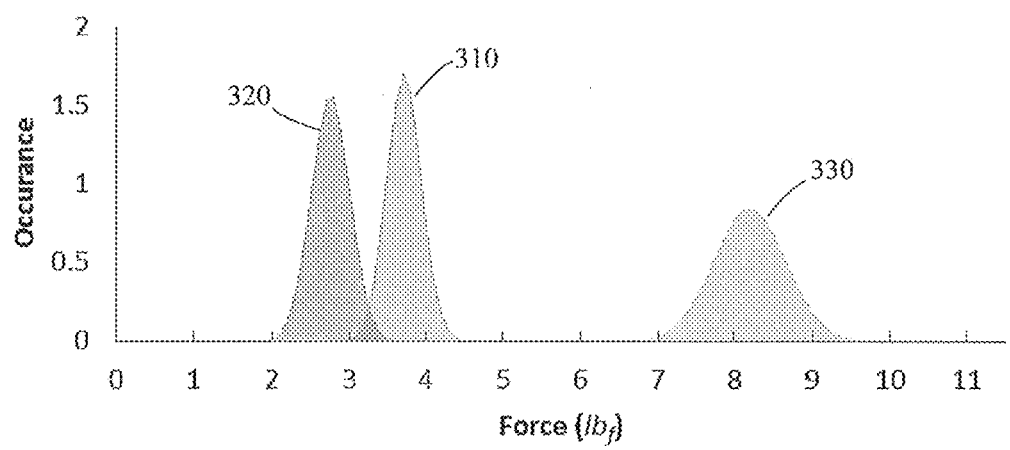
FIG. 3 is a graph illustrating perforation strength and drag force for a 2-ply tissue.
Figure 4:
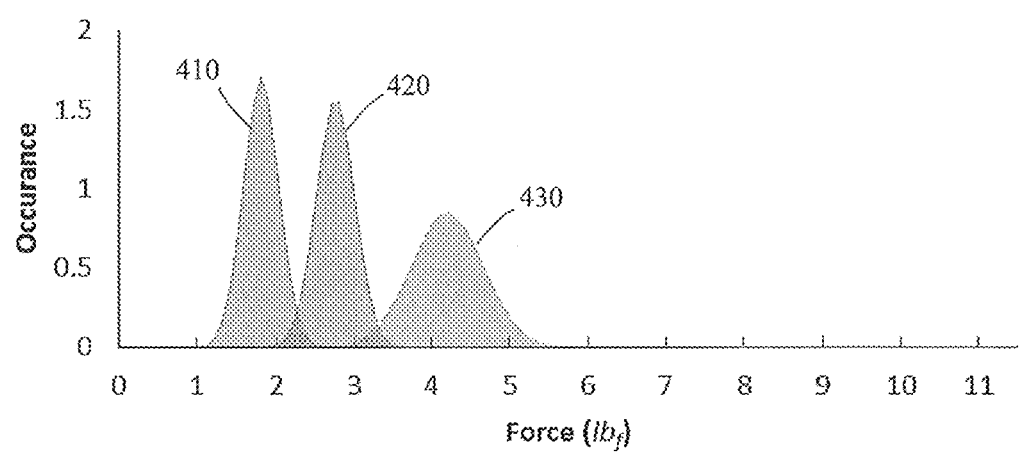
FIG. 4 is a graph illustrating hypothetical perforation strength and drag force for a 2-ply tissue.

A roll of 2-ply HST was perforated using a ¼"×0.040" perforation pattern (0.040" wide tabs spaced ¼" apart). Table 10 below shows the wet perforations strength, drag force, and dry perforation strength for the 2-ply HST substrate. FIGS. 3 and 4 illustrate expected normal distributions of wet and dry perforation strength and drag force. Table 10 provides the raw data.

TABLE 10

Perforation strength

| # | Wet Perf Strength | Drag Force (45 deg., CaviWipe) | Drag Force (45 deg, Multimold) | Dry Perf |
|---|---|---|---|---|
| 1 | 3.79 | 2.67 | 3.34 | 8.64 |
| 2 | 3.47 | 2.95 | 3.07 | 8.59 |
| 3 | 2.68 | 2.62 | 3.28 | 8.61 |
| 4 | 3.77 | 2.95 | 2.85 | 8.89 |
| 5 | 3.96 | 2.98 | 3.15 | 9.51 |
| 6 | 4.34 | 2.8 | 2.83 | 9.69 |
| 7 | 3.17 | 2.64 | 2.59 | 5.82 |
| 8 | 3.25 | 2.82 | 2.81 | 8.56 |
| 9 | 3.88 | 3.19 | 3.11 | 8.43 |
| 10 | 3.79 | 3.03 | 3.16 | 7.92 |
| 11 | 2.79 | 2.51 | 2.61 | 8.13 |
| 12 | 3.21 | 2.55 | 2.96 | 8.15 |
| 13 | 2.93 | 2.33 | 3.01 | 8.25 |
| 14 | 3.08 | 2.63 | 2.74 | 6.99 |
| 15 | 3.64 | 2.48 | 2.7 | 8.84 |
| 16 | 3.29 | 3.08 | 3.23 | 8.87 |
| 17 | 3.85 | 3.07 | 2.55 | 9.25 |
| 18 | 3.36 | 2.61 | 2.91 | 8.98 |
| 19 | 3.64 | 2.58 | 2.69 | 6.78 |
| 20 | 4.15 | 2.39 | 2.23 | 8.23 |
| 21 | 3.3 | 2.45 | 3.2 | 7.82 |
| 22 | 2.87 | 3.05 | 2.48 | 6.96 |
| 23 | 4.21 | 2.47 | 2.64 | 9.97 |
| 24 | 1.11 | 2.33 | 2.86 | 8.37 |
| 25 | 4.11 | 2.4 | 2.92 | 7.62 |
| 26 | 4.14 | 3.14 | 2.6 | 7.35 |
| 27 | 4.55 | 2.81 | 2.71 | 7.36 |
| 28 | 3.98 | 2.93 | 2.67 | 6.82 |
| 29 | 2.93 | 2.9 | 3.06 | 8.18 |
| 30 | 3.18 | 2.95 | 2.88 | 8.45 |
| 31 | 3.95 | 3.05 | 2.77 | |
| 32 | 4.27 | 2.58 | | |
| 33 | 3.57 | 3.23 | | |
| 34 | 4.05 | 2.86 | | |
| 35 | 4.02 | 2.65 | | |
| 36 | 3.79 | 3.16 | | |
| 37 | 3.72 | 2.87 | | |
| 38 | 3.4 | 2.76 | | |
| 39 | 3.23 | 2.66 | | |
| 40 | 3.67 | 2.63 | | |
| 41 | 3.68 | 2.7 | | |
| 42 | 4.17 | 2.82 | | |
| 43 | 4.02 | 2.43 | | |
| 44 | 4.22 | 2.52 | | |
| 45 | 3.91 | | | |
| 46 | 3.67 | | | |
| 47 | 4.4 | | | |
| 48 | 4.15 | | | |
| 49 | 3.94 | | | |
| 50 | 4.24 | | | |

FIG. 3 shows the observed wet perforation strength 310, dry perforation strength 320, and drag force 330 of the 2-ply tissue through a Multi-Mold closure at 45° (commercially available from Multimold Plastics, Inc., Ontario, Canada, part no. SB-128MMSNW). The average wet perforation strength 310 observed was higher than the drag force 320 through the closure. This combination may therefore result in increased dispensing failures (roping).

The dry perforation strength 330 observed was much higher than that required for converting. Conventional wet wipe products may be converted with less than half the observed dry perforation strength. Compared to other substrates, tissue, however, does not have the ability to stretch or elongate. Although the initial peak break force may be high for tissue, the perforation may be broken with much less force if a tear starts on one of the edges. Therefore a perforation pattern with larger tabs (see Constructive Example 12) present on the edge of the tissue may avoid this type of 'zipper' break-out. An alternative method to improve dispensing may be to increase the drag through the closure, which may be accomplished by either increasing the angle of dispense (e.g., 60° or 90°) or modifying the closure orifice.

Example 10

100 wet wipe rolls (donuts) were prepared. The wet wipe roll substrates were 2-ply HST substrates. The wet wipe rolls were perforated to provide individual sheets with dimensions of 7 inches long×5.5 inches wide. A perforation pattern of ¼ inch×0.040 inch was used. Table 11 below provides the properties of the wet wipes.

TABLE 11

Summary of properties

| | |
|---|---|
| Maximum sheet dcount for 120 mm Canister: | 200 wipes |
| Maximum Liquid Loading Ratio (i.e. Absorbency) | 2.0x |
| Liquid Release per Wipe (g): | 1.4 |
| Wipe to Wipe Liquid Retention: | 74% |
| Wet Opacity, MacBeth: | 36 |
| Dry Perforation Strength, Peak (lb$_f$): | $\bar{x}$ = 7.6 ($\sigma$ = 0.9) |
| Wet Perforation Strength, Peak (lb$_f$): | $\bar{x}$ = 3.6 ($\sigma$ = 0.3) |
| Drag Force, Multi-Mold closure, 45° dispense, Peak (lb$_f$): | $\bar{x}$ = 2.9 ($\sigma$ = 0.3) |

Example 11

The absorbent capacity measured according to ASTM International standard D4350 of the inventive multi-ply substrate including papermaking fibers was compared to synthetic substrates. As shown in Table 12, the multi-ply substrate including papermaking fibers had as absorbent capacity which was comparable to synthetic substrates.

TABLE 12

Absorbent capacity

| Substrate | Absorbent capacity (g/g) |
|---|---|
| 2- ply substrate of papermaking fibers (basis weight 26.34 lb/rm) | 10.3 |
| 1-ply substrate of papermaking fibers (basis weight 11.92 lb/rm) | |
| Latex Bond Airlaid Pulp (LBAL) | 10.7 |
| Multi-Bonded Airlaid Pulp (MBAL) | 11.5 |
| Hydroentangled Staple fiber (100% rayon) | 10.5 |

Constructive Example 12

FIG. 4 provides estimated perforation and dispensing data for a 2-ply tissue through a Multi-Mold closure at 45° and ¼"×0.020" perforations. Compared to perforations in Example 9 (¼"×0.040), FIG. 4 shows that reducing the wet perforation strength 410 by roughly half, so that the drag force 420 is higher than the wet perforation strength 410, may improve dispensing. As shown in FIG. 4, the dry perforation strength 430 will also be reduced. Since the perforation strength is substantially linearly proportional to the tab area in the perforation, a pattern of either ¼"×0.020" or ½"×0.040" may be used.

With respect to the above description then, it is to be realized that the optimum dimensional relationships for the parts of the invention, to include variations in size, materials, shape, form, function, and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, various modifications may be made of the invention without departing from the scope thereof and it is desired, therefore, that only such limitations shall be placed thereon as are imposed by the prior art and which are set forth in the appended claims.

What is claimed is:

1. A wet wipe comprising:
a multi-ply tissue impregnated with a wetting composition, the multi-ply tissue not being a synthetic multi-ply tissue and comprising papermaking fibers, being substantially free of synthetic fibers, and having an absorbent capacity of at least about 8 grams of the wetting composition per gram of the dry multi-ply tissue (g/g) as measured in accordance with American Society for Testing and Materials International (ASTM International) standard D4250; and a single ply of the multi-ply tissue having a basis weight of at least 8 pounds per 3,000 square foot ream (lb/rm);
wherein the wet wipe has a liquid release of at least about 0.5 grams of the wetting composition per gram of the multi-ply tissue substrate (g/g).

2. The wet wipe of claim 1, wherein the single ply of the multi-ply tissue has a basis weight in a range between about 10 and about 20 lb/rm.

3. The wet wipe of claim 1, wherein the absorbent capacity is in a range between about 9 and about 11 g/g.

4. The wet wipe of claim 1, wherein the wet wipe is wound into the form of a wet wipe roll.

5. The wet wipe of claim 1, wherein the wet wipe has perforations.

6. The wet wipe of claim 1, wherein the multi-ply tissue comprises two plies.

7. A wet wipe comprising:
a multi-ply tissue impregnated with a wetting composition, the multi-ply tissue not being a synthetic multi-ply tissue and comprising papermaking fibers, being void of synthetic fibers, and having an absorbent capacity of at least about 8 g/g as measured in accordance with ASTM International standard D4250; and a single ply of the multi-ply tissue having a basis weight of at least about 8 lb/rm;
wherein the wet wipe has a liquid release of at least about 0.5 grams of the wetting composition per gram of the multi-ply tissue substrate (g/g).

8. The wet wipe of claim 7, further comprising a wet-strength resin.

9. The wet wipe of claim 8, wherein the wet-strength resin is present in a range between about 0.1 wt. % and about 5.0 wt. % based on the total weight of the papermaking fibers.

10. The wet wipe of claim 7, wherein the wet wipe is disposed within a dispenser having an orifice for accessing the wet wipe.

11. The wet wipe of claim 7, wherein the papermaking fibers are cotton fibers, abaca fibers, kenaf fibers, sabai grass fibers, flax fibers, esparto grass fibers, straw fibers, jute hemp fibers, bagasse fibers, milkweed floss fibers, pineapple leaf fibers, softwood fibers, hardwood fibers, reconstituted cellulose fibers, or any combination thereof.

12. The wet wipe of claim 7, wherein the wet wipe has a liquid release of at least about 0.5 g/g.

13. The wet wipe of claim 7, wherein the wet wipe is wound into the form of a wet wipe roll.

14. The wet wipe of claim 13, wherein the wet wipe has a liquid retention in a range between about 60% and about 95% of the initial liquid absorbed.

15. The wet wipe of claim 7, wherein the multi-ply substrate comprises two plies.

16. A method of making a wet wipe, the method comprising:
forming a multi-ply tissue, the multi-ply tissue not being a synthetic multi-ply tissue and comprising papermaking fibers, being substantially free of synthetic fibers, and having an absorbent capacity of at least about 8 lb/rm as measured in accordance with ASTM International standard D4250; and a single ply of the multi-ply tissue having a basis weight of at least 8 pounds per 3,000 square foot ream (lb/rm); and
impregnating the multi-ply tissue with a wetting composition to form the wet wipe; wherein the wet wipe has a liquid release of at least about 0.5 grams of the wetting composition per gram of the multi-ply tissue substrate (g/g).

17. The method of claim 16, further comprising perforating the multi-ply tissue.

18. The method of claim 16, wherein the multi-ply tissue is formed by folding a single ply of a tissue to combine opposite ends of the tissue.

19. The method of claim 16, further comprising passing the multi-ply tissue through an embossing nip.

* * * * *